United States Patent [19]

Cornell

[11] 4,079,729
[45] Mar. 21, 1978

[54] FLUID COLLECTION WITH VACUUM LOSS INDICATING MEANS

[75] Inventor: William D. Cornell, Ballwin, Mo.

[73] Assignee: Sherwood Medical Industries Inc., St. Louis, Mo.

[21] Appl. No.: 627,822

[22] Filed: Oct. 31, 1975

[51] Int. Cl.[2] ............................................. A61M 1/00
[52] U.S. Cl. ............................. 128/2 F; 128/DIG. 5; 116/114 PV
[58] Field of Search .................. 128/2 F, DIG. 5, 272, 128/276, 275, 214 B, 214 D, 214 E; 206/DIG. 29, 534, 459, 808; 73/388 R, 40, 40.5, 401, 49.2, 49.3; 116/114 P, 114 PV

[56] References Cited

U.S. PATENT DOCUMENTS

| 2,611,481 | 9/1952 | Sargeant et al. | 206/459 |
|---|---|---|---|
| 2,621,268 | 12/1952 | Lindstrom et al. | 73/401 C X |
| 2,821,951 | 2/1958 | Carver | 206/459 |
| 3,334,628 | 8/1967 | Saemann et al. | 116/114 PV X |
| 3,500,821 | 3/1970 | Ogle | 128/DIG. 5 |
| 3,581,743 | 6/1971 | Stein | 128/251 |
| 3,585,984 | 6/1971 | Buchanan | 128/2 F |
| 3,704,096 | 11/1972 | Verses et al. | 206/459 |
| 3,730,168 | 5/1973 | McWhorter | 128/2 F |
| 3,766,918 | 10/1973 | Kessel | 128/276 X |
| 3,783,870 | 1/1974 | Schachet | 128/276 |
| 3,795,147 | 3/1974 | Peterson | 73/49.3 |
| 3,800,780 | 4/1974 | Elliott | 128/2 F |
| 3,833,000 | 9/1974 | Bridgman | 128/276 |
| 3,850,174 | 11/1974 | Ayres | 128/2 F |

FOREIGN PATENT DOCUMENTS

| 1,117,220 | 5/1956 | France | 128/DIG. 5 |
|---|---|---|---|
| 452,335 | 10/1927 | Germany | 128/DIG. 5 |

*Primary Examiner*—J. Reed Fisher
*Attorney, Agent, or Firm*—Stanley N. Garber; William R. O'Meara

[57] ABSTRACT

A blood collection tube useable with a needle holder for drawing blood from a body vessel. The tube has a rubber stopper with an annular axially extending portion in tight sealing engagement within the bore of the tube for maintaining a negative pressure in the tube. An annular groove in the annular portion of the stopper has a vacuum loss indicating member for providing a visual indication that the tube has or does not have a negative pressure therein. The vacuum loss indicating member may be cobalt chloride responsive to atmospheric moisture, a material including methylene blue that is sensitive to oxygen, or a closed-end manometer which has a quantity of liquid therein in a balanced position when normal negative pressure conditions exist in the tube and which moves within the manometer to visually indicate a loss of pressure when such occurs.

18 Claims, 5 Drawing Figures

FLUID COLLECTION WITH VACUUM LOSS INDICATING MEANS

BACKGROUND OF THE INVENTION

This invention relates to fluid collection devices and more particularly to vacuum loss indicating means for a body fluid collection device.

A body fluid collecting device, such as a blood collection tube, has a stopper at one end for maintaining a negative pressure within the tube. The stopper is adapted to be pierced by one end of a double ended needle cannula to effect communication between the negative pressure within the tube and a body vessel that has been pierced by the other end of the needle for drawing blood from the vessel into the tube for test purposes. Should blood fail to be drawn into the tube due to a loss of vacuum in the tube after the needle has been inserted into the patient and the stopper penetrated by the needle, the person withdrawing the blood might assume that the vessel has not been properly penetrated and may make one or more penetrations causing damage to the vessel and surrounding tissue before substituting a new tube. It is therefore desirable to provide some means of indicating, such as by a visual indication, that a negative pressure or partial vacuum does exist in the collection tube before an attempt to use the tube is made.

In U.S. Pat. No. 3,890,955, a vacuum loss indicator is disposed within a collection tube to provide a visual indication that there is or is not a negative pressure in the tube before it is put to use. In this patent, an indicator, such as hemoglobin, is disposed within the tube. Other indicators mentioned include other chemicals, a feather and a ball which will drop at different speeds depending on the air content of the tube, and an object having a pair of vanes and which spins like a helicopter blade in the presence of air in the tube. The disadvantages of such arrangements are that the material collected, such as blood, comes in contact with the indicator and, in some cases, may affect the outcome of the analysis of the blood, or may otherwise contaminate the blood drawn into the tube. In some cases, the type of indicator means limits the type of material that can be satisfactorily drawn into the tube or the type of indicating means may be limited by the material to be drawn into the tube.

SUMMARY OF THE INVENTION

Accordingly, it is an object of the present invention to provide a collection tube having a partial vacuum therein with improved means for indicating the presence or absence of the vacuum within the tube prior to its use. Another object of the present invention is to provide an improved fluid collection tube having indicating means which indicates the presence or absence of a negative pressure within the tube wherein the indicating means cannot affect the fluid drawn into the tube. Still another object of the present invention is to provide a blood collection tube normally having a negative pressure therein for drawing blood into the tube and which is provided with means for indicating the presence or absence of the negative pressure therein and wherein the indicating means does not come in contact with the blood drawn into the tube.

In accordance with one aspect of the present invention, a tube is provided with a stopper for closing one end thereof for maintaining a negative pressure within the tube, and indicating means within the tube and associated with the stopper for indicating the presence or absence of the negative pressure in the tube. In accordance with another aspect of the present invention, a pressure responsive manometer is disposed in a tube normally having a vacuum therein, which manometer provides an indication of the absence or presence of the negative pressure within the tube.

These, as well as other features and advantages of the present invention, will become apparent from the following detailed description and accompanying drawing wherein like reference numerals refer to like parts.

DECRIPTION OF THE PREFERRED EMBODIMENTS

Figure 1:
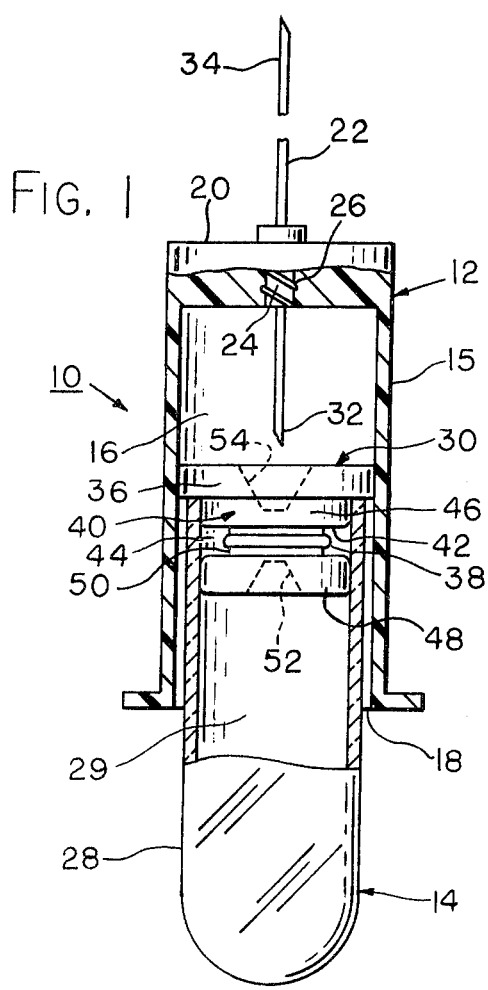
FIG. 1 is an elevational cross-sectional view of a fluid collection device including a collection tube according to a preferred embodiment of the present invention.

Referring now to the drawing, there is illustrated in FIG. 1 a fluid collection unit 10 shown as a blood collection device including a needle holder 12 and a blood collection tube 14 for withdrawing body fluid, such as blood, from a body vessel, such as a vein or artery.

The needle holder 12 includes a cylindrical guide portion 15 having a bore 16 open at the proximal end 18 for slidingly receiving the collection tube 14 and closed at the distal end by an end wall 20 carrying a removable double-ended needle cannula or hypodermic needle 22. The needle cannula 22 is fixed to an externally threaded hub 24 which is threadedly received in a threaded hole 26 in the end wall 20. The holder 12 may be formed of a suitable, relatively hard plastic, such as polypropylene or the like.

The blood collection tube 14 includes a transparent glass test tube 28 having a bore or chamber 29 integrally closed at the proximal end and having a stopper 30 extending into the tube chamber 29 for sealingly closing the distal end of the tube. The stopper 30 is inserted into the tube 28 after air has been evacuated from the tube, the stopped thereafter forming an air-tight seal for the tube preventing the entrance of gas, such as air, into the tube chamber 29. The stopper is preferably made of natural or synthetic rubber which is pierceable by the needle cannula 22.

As seen in FIG. 1, the needle cannula 22 is mounted to the holder 12 along the longitudinal axis of the bore 16 and has a pointed proximal end portion 32 within the bore 16 for piercing the stopper, and a pointed outer distal end portion 34 for insertion into a body vessel. In use, the holder 12 is used to assist in inserting the distal portion 34 of needle 22 into a vessel and, while being held in that position, an evacuated collection tube 14 is inserted into the proximal end of the holder and move distally until the proximal portion 32 of the needle penetrates the stopper 30 and communicates with the interior or chamber 29 of the tube 28 below the stopper.

The stopper 30 is formed with an upper annular flange 36 which is distally of the tube 28 and which has an outer diameter slightly greater than that of tube 28 and which engages the distal end of the tube. The radially outer surface of the stopper flange 36 engages the walls of bore 16 to guide the collection tube 14 for movement toward the end wall 20 so that the proximal portion 32 of the needle penetrates the central portion of the stopper and communicates with the evacuated interior of tube 28. The negative pressure or suction force therein causes blood to be drawn into the tube from the body vessel. The tube 28 is provided with a desired predetermined negative pressure, and the stopper 30 is then inserted into the tube to maintain that negative pressure. The negative pressure employed generally depends upon the desired quantity of blood to be drawn into the tube. After the predetermined amount of blood has been drawn into the tube, the collection tube 14 is removed from the holder 12 so that the blood therein can be subjected to analysis.

In order to avoid the inadvertant use of a collection tube that has lost its desired negative pressure to thereby avoid the previously mentioned undesirable effects resulting from such use, pressure loss indicating means, indicated at 38, is disposed within the interior of chamber 29 of the tube 28. The pressure loss indicator 38 gives a visual indication of the presence or absence of the negative pressure in the tube, as will be more fully explained hereinafter.

The stopper 30 is shown as a single-piece member having an annular plug portion 40 integral with the flange 36. Plug portion 40 extends into tube 28 and sealingly engages the interior walls of the tube to seal the tube against the ingress of gas, such as air into the tube. An annular groove or channel 42 is formed in the periphery of the plug portion 40 and forms an annular, sealed chamber 44 between the inside wall of tube 28 and the walls of the groove 42, the chamber 44 extending 360° around the plug portion. The groove 42 divides the plug portion 40 into integral upper and lower annular plug portions 46 and 48, both of which tightly engage the tube walls to form a seal against the passage of air between the tube and each of these plug portions. Between the plug portions 46 and 48 is an annular, integral neck portion 50, the outer periphery of which forms the bottom of the groove 42. The proximal and distal ends of stopper 30 are provided with central recesses indicated in phantom at 52 and 54, which recesses reduce the amount of material that the needle 30 must pass through in penetrating the stopper.

In manufacturing the collection tube 14, the tube 28 and stopper 30 are, for example, positioned in a vacuum chamber, and the stopper is inserted into the tube after the desired vacuum has been drawn. In this way, the chamber 44 will have a negative pressure substantially the same as that in the interior of the tube below the stopper.

Substantially all air leaks from the atmosphere to the interior of the tube will be caused by the flow of air through the seal, that is, between the stopper and the tube since there is a very small probability of air passing through the glass tube 28 or through the stopper 30. In practically all cases, therefore, any leakage of air into the tube 28 will also have to pass through the seal and indicator chamber 44. The indicator 38 is disposed in the chamber 44 within the tube and will therefore be subjected to any gas or air leaking into the tube.

The indicator 38 may be formed by providing a liquid containing cobalt chloride (cobaltous ion) and water, and applying the liquid around the neck 50 of the stopper to form a layer or ring, and then allowing the ring to dry. The cobalt chloride material may be applied entirely around the neck 50 of the plug for easy viewing through the transparent tube 28. Since cobalt chloride is sensitive to atmospheric moisture, any air leak from the atmosphere under usual condtitions results in air leaking between the stopper 30 and the interior wall of tube 28 and reaching chamber 44, and the moisture content of such air will cause the cobalt chloride in chamber 44 to change composition and color from blue to pink. Thus, a person intending to use a blood collection tube 14 can merely look through the tube 28 at the indicator 38 and determine by the color of the indicator, whether or not a negative pressure exists in the chamber 44. Thus, if the color of the indicator 38 is not blue or is pink, it will be apparent that air has leaked into chamber 44 and possibly also into the portion of chamber 29 below the stopper, and that the particular collection tube should not be used in an attempt to draw blood from a patient.

The indicator 38 may be, instead of the above cobalt chloride composition, a material including methylene blue. For example, a slurry of filter paper fibers in a solution of methylene blue and ethylene diaminetetraacetic acid adjusted to a pH of 10 with sodium hydroxide, may be applied to the neck portion 50 of the stopper 30 and allowed to dry to form a layer or ring in the chamber 44. In this case, oxygen flowing through the seal or between the stopper and the glass tube upon the occurrence of an air leak will combine with the methylene blue and cause a change in color from white to blue, the oxygen changing the composition of the material. In this case, if the color of the indicator is blue, the particular collection tube should not be used.

Figure 2:
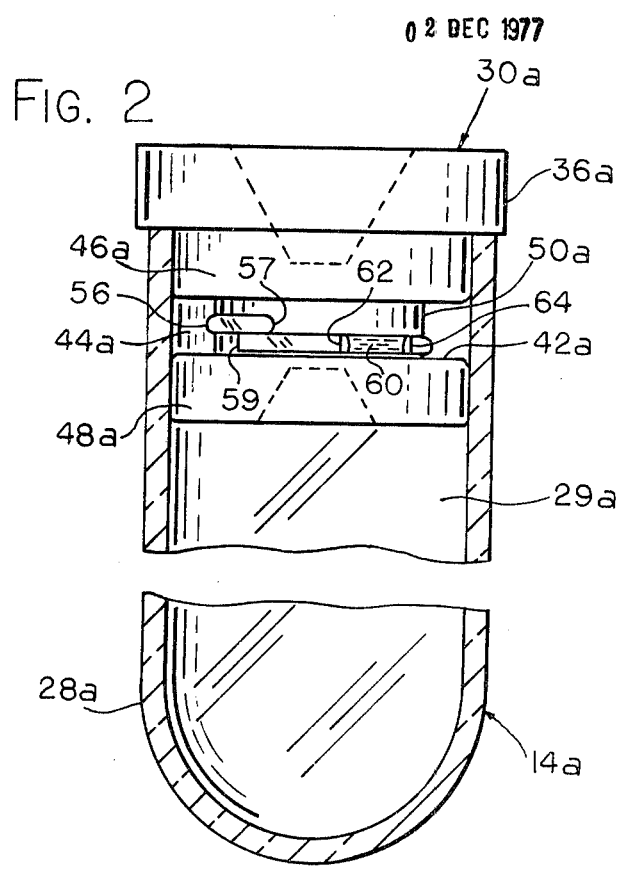
FIG. 2 is an enlarged elevational cross-sectional view of a collection tube in accordance with another embodiment of the present invention.
Figure 3:
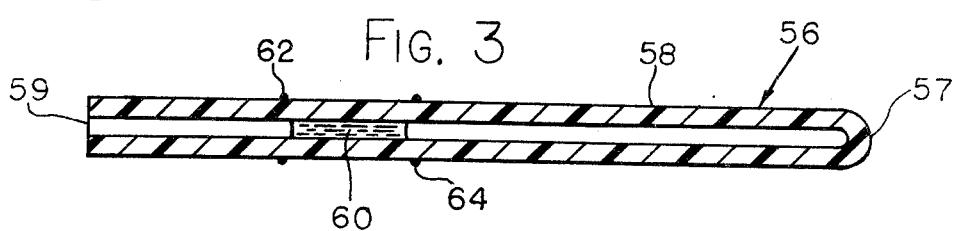
FIG. 3 is a cross-sectional view, on an enlarged scale, of the pressure responsive indicating member of the device of FIG. 2 prior to its assembly in the collection tube.

In FIG. 2, there is shown a collection tube 14a which is identical to collection tube 14 of FIG. 1 except that the negative pressure loss indicator means, indicated at 56, is different from the indicator means 38 of FIG. 1. The indicator means 56 is disposed in an annular indicator chamber 44a formed by a groove 42a in a stopper 30a, which stopper closes the upper end of tube 14a and is identical to the stopper 30 in FIG. 1. In this case, indicator member 56, also seen in FIG. 3, is a manometer in the form of a transparent tube 58 having a movable liquid seal 60 therein. The tube 58 of the liquid manometer 56 is formed of a transparent plastic and is closed at one end 57 and open at the opposite end 59. The manometer tube 58 is shown in FIG. 2 extending around the neck 50a of the stopper. The tube 58 is shown in a straight condition in FIG. 3 but may be permanently bent or given a circular form by stress relieving it while in a coiled or circular condition. The ends of the coiled tube 58 can then be moved apart in order to position the manometer on the neck 50a as shown in FIG. 2. The manometer 56 is held on the stopper by the resiliency of the tube 58.

The open end of the manometer tube 58 is in fluid communication with the sealed chamber 44a that is formed by the walls of the stopper groove 42a and the walls of the tube 28a adjacent the groove. The liquid seal 60 of the manometer may be a mixture of glycerin and a dye or color such that the position of the liquid seal will be readily visually detected by looking through the glass tube 28a and manometer tube 58. The tube 58 may be formed of any suitable plastic, such as clear polypropylene.

As seen in FIGS. 2 and 3, a pair of indicia rings 62 and 64 of a suitable color which can be seen through the tube 28a are axially spaced from each other and predeterminately located on the tube such that when the liquid seal 60 is between the indicia rings, a desired negative pressure exists in the collection tube 14a. The negative pressures on the opposite sides of the glycerin seal 60 are substantially equal so that the seal will be located between the indicia rings 62 and 64 when the desired vacuum or normal negative pressure exists in the collection tube. If the liquid seal is seen to be between the rings 62 and 64, the pressure within the indicating chamber 44a and in the tube 28a below the stopper will be at the desired normal negative pressure value and the collection tube 14a will be functional. However, if the user selects a blood collection tube and sees that the glycerin seal 60 is to the right of the ring 64, as viewed in FIG. 2, that is, if it has moved toward the closed end of the manometer tube 56, the user will know that the vacuum in the indicator chamber 44a and possibly also in the portion of the collection chamber 29a below the stopper has been lost due to air leaking through the tube-to-stopper seal. In such case, the user, of course, should not attempt to use the particular blood collection tube.

Figure 4:
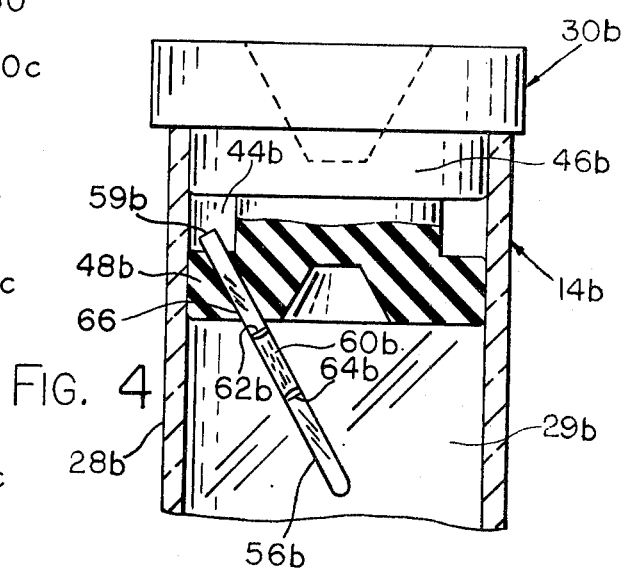
FIG. 4 is a fragmentary elevational cross-sectional view of a collection tube in accordance with another emobodiment of the present invention.

FIG. 4 illustrates another embodiment wherein a collection tube 14b is provided with a stopper 30b for maintaining a negative pressure in a glass tube 28b having the lower end thereof (not shown) closed. A straight liquid manometer 56b extends angularly through an opening 66 in the lower plug portion, indicated at 48b, with the open end 59b disposed within the indicator chamber 44b of the stopper but with the manometer extending below the stopper. The manometer 56b may be identical to the manometer shown in FIG. 3. The manometer 56b may be formed of any suitable material, such as a rigid transparent material, for example, glass or hard plastic. The manometer is held in place in the stopper by a friction fit or may be cemented in the opening 66 where desired.

As in the embodiment of FIG. 2, the manometer 56b of FIG. 4 is positioned in the collection tube with the open end 59b in fluid communication with chamber 44b between portions 46b and 48b, and with the liquid seal 60b located between the indicia 62b and 64b with pressure on opposite sides of the seal 60b equal when the pressure in chamber 44b is at the desired predetermined value. Should air leak between the tube 28b and stopper 30b, the negative pressure in indicator chamber 44b will decrease so that the pressure on opposite sides of liquid seal 60b will become unequal and the seal 60b will move downwardly past indicia 64 toward its lower closed end. This position of seal 60b, of course, will provide an indication that air may have leaked also into the lower portion of the collection tube 14b and that the collection tube should not be used in an attempt to draw blood.

Figure 5:
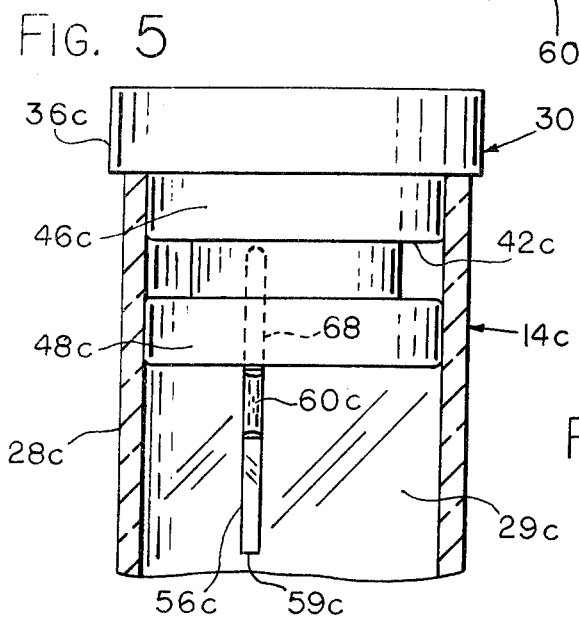
FIG. 5 is a fragmentary cross-sectional view of a collection tube in accordance with still another embodiment of the present invention.

FIG. 5 shows still another embodiment wherein a similar stopper 30c has a straight liquid manometer 56c inserted vertically into an opening 68 in the lower portion of the stopper and frictionally and/or adhesively secured therein. A liquid seal 60c appears below the tube, as in the case of the embodiment shown in FIG. 4. In FIG. 5, however, the liquid manometer 56c has its open end 59c in direct communication with the main portion or collection portion of the collection chamber 29c below the stopper. In this case, the liquid seal of manometer 56c will rise toward its closed upper end upon the occurrence of an air leak into the collection chamber to provide a visual indication of an air leak if such occurs. This embodiment is useful in cases where the fluid drawn into the collection tube does not enter the manometer tube or where no undesirable effect results from the fluid contacting the manometer liquid. In this embodiment, the stopper 30c need not be provided with the groove 42c since the open end of the manometer is in direction communication with the chamber 29c at a point below the stopper.

In the embodiment illustrated in FIG. 4, the manometer 56b and stopper 30b may be constructed and arranged such that the liquid seal 60b is within the stopper and out of view of the user when a desired negative pressure exists in the collection tube, and moves into sight below the stopper only when the negative pressure has been lost. In the embodiment of FIG. 5, the manometer 56c may be positioned so that the liquid seal 60c is in view when a negative pressure exists in the collection tube 14c and moves into the stopper 30c and out of view upon the occurrence of a loss of negative pressure in the collection tube.

In manufacturing collection tubes in which the indicator is moisture sensitive, such as one employing cobalt chloride, a high vacuum may be initially drawn. Then, the tube can be back filled with a moisture free gas, such as dry air, to the desired partial vacuum before the stopper and indicator are inserted in the tube. Where the indicator is sensitive to oxygen, such as one containing methylene blue, the tube may be back filled with a gas, such as nitrogen, that does not affect the indicator.

It will be apparent that in the embodiments illustrated in FIGS. 1 and 2, the fluid drawn into the collection tube cannot be affected by the indicator means. For example, in these embodiments, the lower plug portion (48, 48a) of the stopper completely seals the indicator means (38, 56) from the contents or blood drawn into the tube. Thus, various types of materials and devices may be employed in the stopper groove for providing an indication of the presence or absence of the negative pressure within the tube regardless of whether or not they are compatible with the material or fluid drawn into the tube since they do not come into contact with each other. In the construction shown in FIG. 4, the material drawn into the collection tube may come into contact with a portion of the manometer tube, but the manometer tube may be made from a material, such as glass or plastic, that will not affect the fluid or blood drawn or the testing of the fluid. In any event, the liquid manometer seal 60b cannot come in contact with the blood drawn into the collection tube since the manometer tube is in sealing engagement with the stopper where it passes through it. Also, in all of the embodiments shown, the pressure loss indicating means is conveniently connected to and carried by the stopper so that when the stopper is removed from a filled collection tube, the indicating means is also removed from the tube.

As various changes could be made in the above constructions without departing from the scope of the invention, it is intended that all matter contained in the above description and shown in the accompanying drawing shall be interpreted as illustrative and not in a limiting sense.

What is claimed is:

1. A body fluid collection device comprising a collection tube having one end closed, stopper means extending into said tube closing the opposite end thereof, said stopper means having a pair of axially spaced portions sealingly engaging axially spaced portions of the interior wall of said tube forming a sealed chamber including interior wall portions of said tube between said axially spaced portions thereof and said stopper means, said chamber and the interior of said tube below said stopper each normally having a negative pressure therein, and negative pressure loss indicating means disposed in fluid communication with said chamber for indicating a negative pressure loss therein.

2. The device of claim 1 wherein said negative pressure loss indicating means comprises a material changeable in color in response to the ingress of gas from the exterior of said tube.

3. The device of claim 2 wherein said negative pressure loss indicating means comprises a material changeable in color in response to the presence of moisture resulting from air leaking into said chamber.

4. The device of claim 3 wherein said meterial comprises cobalt chloride.

5. The device of claim 2 wherein said negative pressure loss indicating means comprises a material changeable in color in the presence of a gas present in the atmosphere.

6. The device of claim 5 wherein said material comprises a compound including methylene blue.

7. The device of claim 1 wherein said negative pressure responsive means comprises a manometer responsive to a change in pressure in said chamber to provide a visual indication thereof.

8. The device of claim 7 wherein said manometer comprises a manometer tube having a closed end, and an open end in fluid communication in said chamber, and a liquid seal in said manometer tube movable in response to a change in pressure in said chamber.

9. The device of claim 8 wherein said manometer tube is wholly within said chamber.

10. The device of claim 7 wherein said manometer tube extends through a portion of said stopper and has its open end in fluid communication with said chamber and said lower end below said stopper.

11. The blood collection device of claim 1 wherein said stopper means includes a distal flange integrally connected with said axially spaced portions and disposed distally of the distal end of said tube, said flange having a greater outer diameter than that of said tube.

12. The blood collection device of claim 1 wherein said indicating means includes a liquid manometer tube having an open end, a liquid seal therein, and a closed end, said open end of said liquid manometer tube is in direct fluid communication with the interior portion of said tube below said stopper.

13. The device of claim 1 wherein said sealed chamber is generally annular and extends 360° around said stopper means.

14. The device of claim 1 wherein said stopper means comprises a resilient stopper which is penetratable by a needle cannula for drawing blood directly into the interior of said tube below said stopper, said chamber being sealed from the interior of said tube below said stopper.

15. A blood collection device comprising a transparent collection tube closed at one end, a single-piece stopper penetratable by a needle cannula for drawing blood directly into the interior of said tube below said stopper, said stopper having a portion thereof extending into said tube to close the opposite end of said tube, said stopper portion having a generally annular peripheral groove therein, axially spaced annular sealing portions on axially opposite sides of said groove sealingly engaging axially spaced interior wall portions of said tube, and a neck portion connecting said sealing portions together and having an outer surface defining the radially inner wall of said groove, other portions of the interior wall of said tube between said interior wall portions forming with said groove a generally annular sealed chamber normally having a negative pressure therein and sealed from the interior of said tube below said stopper, and negative pressure loss indicating means extending at least partially around said neck portion and in fluid communication with said chamber and providing a visual indication of a loss of negative pressure in said chamber if such a loss occurs.

16. The blood collection tube of claim 15 wherein said negative pressure loss indicating means extends completely around said neck.

17. The blood collection tube of claim 15 wherein said negative pressure loss indicating means comprises a material adhering to said neck and changeable in color in response to the leakage of air from the atmosphere to said groove.

18. The blood collection tube of claim 15 wherein negative pressure loss indicating means comprises a liquid manometer closed at one end and open at the opposite end and having a movable liquid seal therebetween, said manometer being disposed in said tube with said open end in direct fluid communication with said groove, said manometer having substantially equal negative pressures on the opposite sides of said liquid seal under normal negative pressure conditions in said groove, said liquid seal being movable toward the closed end of said manometer tube in response to air leaking into said groove to provide a visual indication of the same.

* * * * *